United States Patent [19]

Hershberger et al.

[11] Patent Number: 4,710,466
[45] Date of Patent: Dec. 1, 1987

[54] METHOD OF CLONING MODIFIED STREPTOMYCETES DNA

[75] Inventors: Charles L. Hershberger, New Palestine; Jeffrey L. Larson, Indianapolis, both of Ind.

[73] Assignee: Eli Lilly and Company, Indianapolis, Ind.

[21] Appl. No.: 654,063

[22] Filed: Sep. 25, 1984

[51] Int. Cl.$^4$ .................. C12P 19/34; C12N 15/00; C12N 1/20; C12N 1/00; C12R 1/465

[52] U.S. Cl. ................... 435/91; 435/172.1; 435/172.3; 435/253; 435/886; 435/320; 935/31; 935/55; 935/56; 935/57; 935/58; 935/73; 935/75; 935/79; 935/80

[58] Field of Search .............. 435/68, 70, 71, 91, 435/172.3, 886, 317, 172.1; 935/55-58, 73, 75, 79, 80, 31

[56] References Cited

PUBLICATIONS

*The Merck Index,* 9th Edition, Windholz et al (ed.), 1976, Merck & Co., Inc., Rahway, N.J., pp. 1260 and 1261.

Horinouchi et al, "Cloning of a Pleiotropic Gene That Positively Controls Biosynthesis of A-Factor, Actinorhodin, and Prodigiosin in *Streptomyces coelicolor* A3(2) and *Streptomyces lividans*", J. Bacteriol. 155: 1238 (1983).

Galleron, C., 1984, Origins of Life 13: 195-203.
Rae, P., 1976, *Science 194:* 1062-1064.
Bull et al, 1984, *Nature 310:* 701-704.
Maniatis, et al., 1978, *Cell 15:* 687-701.
Shedlovsky et al. 1963, *Proc. Natl. Acad. Sci. 50:* 300-305.
Fleischman, R., et al., 1976, *J. Biol. Chem. 251:* 1561-1570.
Stonesifer, et al., 1986, Mol. Gen. Genet., 202:348-355.
Birmingham et al., 1986, Mol. Gen. Genet., 204:532-539.
Larson et al., 1986, Plasmid, 15:199-209.

*Primary Examiner*—James Martinell
*Attorney, Agent, or Firm*—Gerald V. Dahling; Leroy Whitaker

[57] ABSTRACT

A method of cloning endogenously modified Streptomycetes DNA, which is normally rejected by restrictionless heterospecific hosts, is disclosed. The method uses bacteriophage lambda to construct a genomic library of modified Streptomycetes DNA; such lambda-containing Streptomycetes DNA is replicated to provide a source of non-modified Streptomycetes DNA. This non-modified DNA is subcloned into a selectable cloning vector and used to transform restrictionless hetero-specific hosts. The transformants can then be screened for clones containing genes of interest.

9 Claims, 2 Drawing Figures

Restriction Site and Functional Map of Plasmid pHJL210
(~11.2 kb)

Restriction Site and Functional Map of
Plasmid pHJL240
(~24.4 kb)**

METHOD OF CLONING MODIFIED STREPTOMYCETES DNA

Antibiotics are economically-important chemicals produced by a variety of prokaryotic and eukaryotic microorganisms. The prokaryotic Streptomycetes produce over seventy percent of all known antibiotics. Therefore, it is desirable to develop cloning systems and vectors that are applicable to that industrially important group.

The present invention provides a method of cloning endogenously modified Streptomycetes DNA in restrictionless heterospecific hosts in which said modified DNA is incompatible. The invention comprises constructing a genomic library of modified Streptomycetes DNA, said library comprising one or more modified Streptomycetes DNA-containing bacteriophage cloning vectors in a compatible bacterial host cell; growing said host cell under conditions suitable for replication of said Streptomycetes DNA; incorporating said Streptomycetes DNA, or a portion thereof, after the DNA replication step, into a recombinant DNA cloning vector that is functional and selectable in said heterospecific host cell; and transforming said heterospecific host cell with said vector containing the incorporated Streptomycetes DNA.

The present invention solves a general, but not universal, phenomenon concerning Streptomycetes DNA. Numerous species of Streptomycetes may endogenously modify nucleotides which interferes with direct attempts to clone such modified Streptomycetes DNA. This cloning barrier is overcome in the present method through the substitution of endogenously modified Streptomycetes DNA with non-modified Streptomycetes DNA. The non-modified DNA can then be subcloned into a selectable cloning vector and used to transform restrictionless heterospecific hosts. Prior to the date of this invention, such endogenously modified Streptomycetes DNA was unavailable for use in molecular cloning, thus the present invention represents a significant advance in the technical art.

The method of the present invention provides for the isolation and characterization of Streptomycetes DNA from organisms which contain endogenously modified DNA. As recognized in the art, the word Streptomycetes is synonymous with Streptomyces and designates the genus. Gene cloning and expression of products in Streptomycetes are highly advantageous since the organisms are substantially non-pathogenic and ordinarily do not produce endotoxins. In addition, Streptomycetes have been extensively studied and are well known and understood in the antibiotic and fermentation industries. To facilitate the development of industrial strains with increased antibiotic yield or the production of new antibiotics, however, the cloning of genes within and between Streptomycetes is required to study the expression of particular genes. To achieve this, the present method for molecular cloning involving the transfer of genes between unrelated and incompatible Streptomycetes was developed.

The invention further provides a method of cloning *Streptomyces fradiae* DNA in heterospecific hosts. *Streptomyces fradiae* is thought to be a strain which modifies its DNA, a factor which has contributed to the difficulty associated with attempts to clone *S. fradiae* DNA. *Streptomyces fradiae* is an economically important species for it produces the macrolide antibiotic, tylosin. This antibiotic is used extensively in animal nutrition as a feed additive and as a therapeutic substance in treatment of mycoplasmosis in poultry and livestock. Tylosin has also been reported to inhibit the growth of spirochetes, protozoa and mouse oxyurids. Heretofore, the development and exploitation of recombinant DNA techniques in the above organism has been retarded and time-consuming because of the general lack of efficient cloning systems available to clone this endogenously modified Streptomycetes DNA. The present invention provides a cloning system that successfully replicates *S. fradiae* DNA and thus allows for the commercial development of that industrially useful strain.

For purposes of the present invention as disclosed and claimed herein, the following terms are as defined below.

Recombinant DNA Cloning Vector - any autonomously replicating or integrating agent, including but not limited to plasmids, comprising a DNA molecule to which one or more additional DNA segments can or have been added.

Restriction Fragment—any linear DNA generated by the action of one or more restriction enzymes.

Restrictionless Host—For purposes of the present invention, a restrictionless host is a cell from a strain that lacks restriction enzymes which cut or degrade plasmid DNA upon transformation.

Library—a collection of individually cloned fragments of DNA, which together represent an entire genome or a portion of a genome.

Transformation—the introduction of DNA into a recipient host cell that changes the genotype and consequently results in a change in the recipient cell.

Transformant—a recipient host cell that has undergone transformation.

Modified DNA—a DNA from one cell that is prevented from replicating in a related, but not identical, cell; such DNA may incorporate nucleotides other than the normal adenine, guanine, cytosine and thymine during DNA replication or may be enzymatically modified after DNA synthesis is complete.

Incompatible—DNA which appears to be rejected and not capable of replicating in a host cell.

Endogenous—orginating within the organism.

Ap ®—the ampicillin resistant phenotype.

NM ®—the neomycin resistant phenotype.

Tyl ®—the tylosin resistant phenotype.

Ts ®—the thiostrepton resistant phenotype.

DETAILED DESCRIPTION OF THE INVENTION

Figure 1:
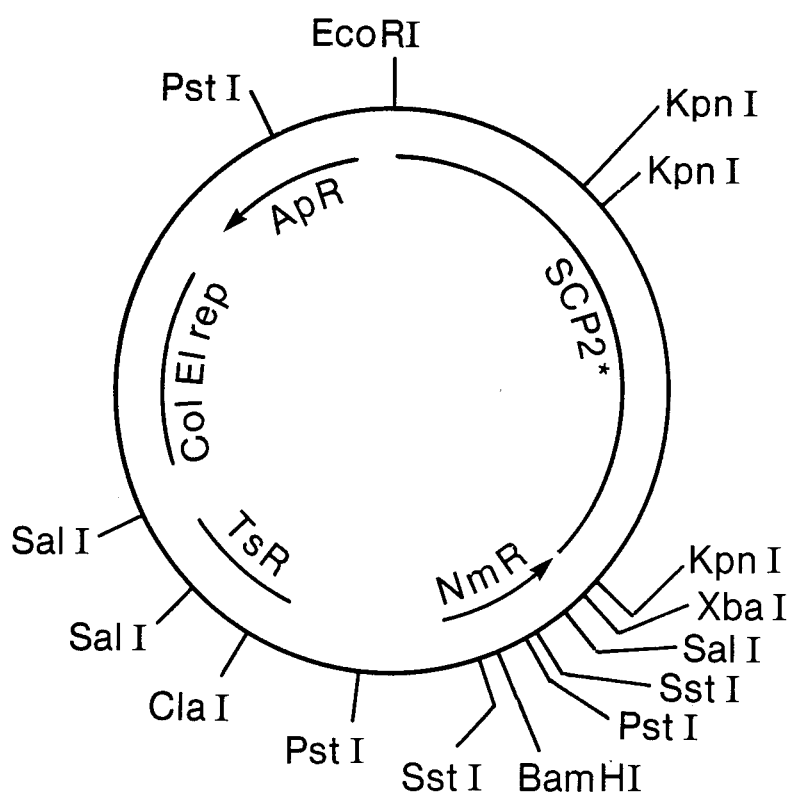
FIG. 1 is a restriction site and functional map of plasmid pHJL210.

The present invention comprises a method of cloning endogenously modified Streptomycetes DNA in a restrictionless heterospecific host cell in which said modified DNA is incompatible, said method comprising:

(a) constructing a genomic library of modified Streptomycetes DNA, said library comprising cloned modified Streptomycetes DNA cloned into a bacteriophage cloning vector and propagated in a compatible bacterial host cell;

(b) growing said host cell under conditions suitable for replication of said Streptomycetes DNA;

(c) incorporating said Streptomycetes DNA, or a portion thereof, after step (b) into a recombinant DNA cloning vector that is functional and selectable in said heterospecific host cells; and (d) transforming said heterospecific host cells with said vector containing the incorporated Streptomycetes DNA of step (c).

Numerous attempts to clone *Streptomyces fradiae* DNA on plasmid vectors in heterospecific hosts have resulted in failure. *Streptomyces fradiae* is an old and well-known strain which is available to the public under the accession number ATCC 19609 and is on deposit and made part of the American Type Culture Collection, 12301 Parklawn Drive, Rockville, Md. 20852. Although *S. fradiae* (ATCC 19609) was used and exemplified in the present invention, any other *S. fradiae* strain can be used and is within the scope of the present invention. Nucleotide analysis data indicate that the DNA from *S. fradiae* contains a modified nucleotide in place of deoxycytidylate. It may be that the modified DNA is rejected and is then incompatible in a variety of hosts because of an undetermined species specific mechanism or mechanisms. The rejection is species specific as shown by observation that *S. fradiae* DNA can be cloned into *S. lividans* but it is rejected and not readily cloned in both *E. coli* and *S. griseofuscus*. It should be understood that the mechanics of the proposed modification and host rejection are not relevant for purposes of the present invention but are offered solely as one possible explanation for the difficulty associated with attempts to clone *S. fradiae* DNA.

More particularly, high molecular weight *Streptomyces fradiae* DNA was independently fragmented with either Hae III or Alu I restriction enzyme to generate molecules with blunt ends. These fragments were analyzed by agarose gel electrophoresis and those in the size range of 10–25 kilobases (kb) DNA were pooled and rendered EcoRI resistant by treatment with EcoRI methylase. Synthetic DNA linkers bearing EcoRI recognition sites were covalently attached by bluntend ligation using T4 ligase. Cohesive ends were then generated by digestion with EcoRI restriction enzyme. These molecules were covalently joined to prepared lambda Charon 4 EcoRI arms, and the hybrid DNA molecules were then packaged into viable phage particles in vitro. Following amplification by growth in *E. coli*, a lysate was obtained, consisting of a library of recombinant clones.

The present invention employs the lambda Charon 4 bacteriophage in the construction of a phage library. However, any bacteriophage vector that is capable of in vitro packaging such as, for example, any of the vectors from the Charon series, the lamoda gt series, MBL series or lambda Wes series, can be substituted for the lambda Charon 4 vector presently exemplified. Additionally, the various enzymatic digestions and linkers used to construct the library are merely illustrative of the present invention and are not meant to limit the scope of the invention.

Due to the difficulty associated with attempts to clone *Streptomyces fradiae* DNA on plasmid vectors, the above construction of a *S. fradiae* phage library was a necessary preliminary step wherein non-modified Streptomycetes DNA was substituted in vivo for the endogenously modified Streptomycetes DNA. Thereafter, the DNA from the phage library was subsequently digested with EcoRI restriction enzyme and ligated to dephosphorylated and EcoRI-digested plasmid pHJL210, a moderately high copy number *E. coli*-Streptomycetes shuttle vector. This plasmid can be conventionally isolated from *E. coli* K12 C600R$_k$-M$_k$-/pHJL210, a constructed strain deposited and made part of the stock culture collection of the Northern Regional Research Laboratory, Peoria, Ill. 61604. It is available to the public as a source and stock reservoir of the plasmid under the accession number NRRL B-15824. *Streptomyces griseofuscus* was subsequently transformed with the hybrid plasmid to prepare a genomic library of *S. fradiae* in this heterospecific host. The library was screened for tylosin resistant clones to verify that the library was useful for isolating recombinant clones.

The construction of a genomic library of *Streptomyces fradiae* DNA allows for the screening and isolation of resistance genes useful as a selectable marker. The development and exploitation of recombinant DNA technology in Streptomycetes is dependent upon the availability of selectable genetic markers on suitable cloning vectors. This development has been somewhat retarded by the low number of selectable markers presently available for use in Streptomycetes. The present invention is useful and especially important in that it expands the number of selectable markers suitable for such use.

*Escherichia coli* K12 C600R$_k$-M$_k$- /pHJL210 (NRRL B-15824) and *E. coli* K12 C600R$_k$-M$_k$-(ATCC 33525) can be cultured in a number of ways using any of several different media. Carbohydrate sources which are preferred in a culture medium include, for example, glucose and glycerol, and nitrogen sources include, for example, ammonium salts, amino acid mixtures, and peptones. Nutrient inorganic salts are also incorporated and include the customary salts capable of yielding magnesium, sodium, potassium, ammonium, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Escherichia coli* K12 C600R$_k$-M$_k$-/pHJL210 can be grown under aerobic culture conditions over a relatively wide pH range of about 6.5 to 7.5 at temperatures ranging from about 25° to 42° C. For the production of plasmid pHJL210 in the greatest quantity, however, it is desirable to start with a culture medium at a pH of about 7.2 and maintain a culture temperature of about 37° C. Culturing the *E. coli* cells under the aforementioned conditions, results in a reservoir of cells from which the plasmid pHJL210 is isolated by techniques well known in the art.

The following examples further illustrate and detail the invention disclosed herein. Both an explanation of and the actual procedures for constructing the invention are described where appropriate.

EXAMPLE 1

Preparation of Lambda Charon 4 DNA

A. Preparation of Lambda Charon 4 Vector

An overnight culture of *Escherichia coli* K12 C600R$_k$-M$_k$-(ATCC 33525) was grown at 37° C. in 10 ml. of T broth (10 gm. Bacto-Tryptone, 5 gm. yeast extract, 5 gm. NaCl and distilled water to 1 liter, pH 7.0) supplemented with maltose (20% maltose to 0.2%) and MgSO$_4$ (1M MgSO$_4$ to 10 mM). Supplemented broth is designated TMM. A phage stock of Charon 4, a standard *E. coli* K12 lambda cloning vector (DeWet, et al., 1980, J. Virol. 33:401-410 or available through Dr. F. Blattner, Laboratory of Genetics, University of Wisconsin-Madison, Madison, Wis. 53706) was serially diluted and 0.1 ml. of the individual phage dilutions were added to 0.1 ml. of a 1/10 dilution of the *E. coli* culture grown in TMM. These cultures were then incubated at 37° C. for 20 minutes. After 3 ml. of TM top agar (T broth plus 10 mM MgSO$_4$ and 0.7% agar) were added, the cultures were plated on T agar supplemented with MgSO$_4$ (T broth plus 1.5% agar and 10 mM MgSO$_4$) A plate containing ~20,000 pfu (placque-forming units) was selected and flooded with 5 ml. of lambda buffer (6.35 gm. Tris-HCl, 1.18 gm. Tris base, 2.46 gm. MgSO$_4$.7H$_2$O, 5.84 gm. NaCl and distilled water to 1 liter). The plate was scraped into a 50 ml. Sorvall tube and after the addition of 0.1 ml. CHCl$_3$, the tube was centrifuged at 4,000 rpm for 10 minutes. The supernatant was collected in a fresh tube and 0.5 ml. CHCl$_3$ was added. It should be noted that 3-5 lysates may be made to obtain the proper titer.

B. Preparation of Phage Lysate

A 20 ml. culture of *E. coli* K12 C600R$_k$-M$_k$-(ATCC 33525) was grown in TMM broth at 37° C. overnight. This culture was mixed with 10$^9$ pfu of Charon 4 (from the plate lysates of Example 1A and titered according to conventional methods) and incubated at 30° C. for 10 minutes without shaking. The incubated mixture was divided in half and each half was added to a 1 liter flask containing 500 ml. of T broth supplemented with 1M MgSO$_4$ to a final concentration of 10 mM MgSO$_4$ and shaken at 37° C. until lysis (about 3-8 hours).

After lysis, DNase I [(5 mg./μl. in·50 mM Tris-HCl pH 8.0), obtained from Worthington Diagnostic, Freehold, N.J. 07728 ] was added to a final concentration of 1 mg./ml. per flask and the flasks were shaken for 15 mintues. Next, 7.9 gm. NaCl/100 ml. was added to each flask and shaken into solution. After 0.2 ml. of chloroform was added per flask, the contents were transferred to Sorvall centrifuge bottles and spun in a GSA rotor at 4,000 rpm for 10 minutes. After pooling the supernatants, polyethylene glycol 6000 (obtained from Sigma) was added to a final concentration of 100 gm./l., shaken into solution and placed in an ice bath for 1 hour.

Aliquots of this solution were transferred to Sorvall bottles and the precipitates were collected by centrifugation in a GSA rotor for 10 minutes at 6,000 rpm. All pellets were resuspended in a total volume of 15 ml. of lambda buffer and transferred to a 50 ml. Sorvall tube containing 15 ml. of chloroform and vortexed before centrifugation at 4,000 rpm for 10 minutes.

After the upper aqueous phase was collected, cesium chloride (0.814 gm/ml) was added and adjusted to obtain a refractive index of 1.3809. The solution was transferred to Beckman ultracentrifuge tubes and spun to equilibrium (18 hr., 50,000 rpm). The phage band was extracted with a needle and syringe and dialyzed against 2 liters of lambda buffer for 4-8 hours. After the approximate DNA concentration was determined, lambda DNA was extracted by the addition and gentle mixing of an equal volume of buffer saturated (50 mM Tris-HCl pH 8.0) phenol [Ultra-pure obtained from Bethesda Research Laboratory (BRL) Gaithersburg, Md. 20877]. The phases were separated by centrifugation in a Sorvall centrifuge and the aqueous layer removed and mixed with an equivalent volume of ether. The phases were again separated by centrifugation and the ether layer removed and discarded. After the ether extraction step was repeated, the λ DNA solution was made 0.3M NaOAc by the addition of 3M NaOAc pH 8.0. The DNA was precipitated by the addition of 2 volumes cold ethanol and stored overnight at −20° C. The DNA was collected by centrifugation (15,000 rpm, 15 mins., Sorvall tubes), washed once with 70% ethanol and air dried. This DNA pellet was resuspended in 500 μl. TE to a final concentration of ~400 μg./ml.

C. Preparation of Charon 4 EcoRI Arms

To obtain both the left and right arms of Charon 4, 250 μl. of Charon 4 DNA (100 μg.), 30 μl. 10X EcoRI buffer (1000 mM Tris-HCl pH 7.5, 500 mM NaCl, and 50 mM MgCl$_2$), and 10 μl. distilled water were digested with 10 μl. [(100 units) New England Biolabs, Inc., 32 Tozer Road, Beverly, Mass. 01915] EcoRI enzyme for 2 hours at 37° C. An additional 10 μl. of EcoRI enzyme was added and incubated for another hour. The reaction was terminated by increasing the temperature to 70° C. for 10 minutes. An equal volume of buffer saturated phenol was mixed in and the phases separated by centrifugation in a microfuge. The aqueous layer was removed and extracted twice with ether as described in the preceding example.

The DNA suspension was divided in half and added to two SW40 tubes containing 10-40% w/v sucrose (in 1M NaCl, 20 mM Tris-HCl pH 8.0, and 5 mM EDTA) gradients containing 2 μg./μl. ethidium bromide essentially as described in Maniatis et al., 1982, Molecular Cloning, Cold Spring Harbor Laboratory, Cold Spring Harbor, N.Y. After running in a Beckman SW40 rotor for 15 hours at 25,000 rpm at 5° C., the bands were visualized by UV light and the four visible bands extracted with a syringe and needles. The ethidium bromide was extracted with n-butanol and the resulting DNA examined by agarose gel electrophoresis (AGE). The two bands representing the left and right arms of Charon 4 were mixed equimolar, diluted in half, precipitated by the addition of two volumes of ethanol and stored at −20° C. overnight. The DNA precipitate was collected by centrifugation in an HB4 rotor (Sorvall tube, 12,000 rpm, 30 min.) and then resuspended in 100 μl. TE to a final concentration of 0.174 μg./μl. Charon 4 arm DNA.

EXAMPLE 2

Preparation of *Streptomyces fradiae* DNA

A. Culture of *Streptomyces fradiae*

An overnight culture of *Streptomyces fradiae* was grown at 30° C. in 10 ml. of trypticase soy broth (TSB*) by inoculating a single colony into 10 ml. of broth and homogenizing this solution three times until the colony is disrupted. The 10 ml. overnight culture was homogenized and used to inoculate a flask containing 500 ml. of TSB supplemented with glycine to a final concentration of 0.4%. The culture was grown for 48 hours at 30° C. and the mycelia collected by centrifugation at 10,000 rpm for 15 minutes in Sorvall centrifuge bottles using a RC-5 Sorvall and a GSA rotor. About 50 grams of wet mycelia were produced. *Trypticase soy broth is obtained from Baltimore Biological Laboratories, P.O. Box 243, Cockeysville, Md. 21031 or Difco Laboratories, Detroit, Mich.

The cell pellet was resuspended in 500 ml. of Tris-sucrose (10 mM Tris-HCl pH 8.0/1.0 mM EDTA/25% sucrose). Next, the suspension was supplemented with 250 ml. of 0.25M EDTA (pH 8.0) and 250 ml. of lysozyme solution [10 mg./ml. lysozyme (Calbiochem) in Trissucrose solution]. This mixture was incubated at room temperature for 15 minutes and then 50 mg. of proteinase K (Beckman) was added and the suspension incubated for an additional 30 minutes. About 50 ml. of a 20% w/v solution of sodium dodecyl sulfate (ultrapure obtained from Gallard-Schlesinger Chemical Mfg. Corp., 584 Mineola Place, New York City, N.Y. 11514) was added, gently mixed and then the lysed cells were incubated at 55° C. for 30 minutes. After 250 ml. of 5M NaCl was gently mixed into the lysed cell solution, the suspension was transferred to Sorvall centrifuge tubes (~40 ml./tube) and placed on ice for 2 hours. The solution was centrifuged at 15,000 rpm for 20 minutes in a Sorvall SS34 rotor and centrifuge. The supernatants were pooled together (~700 ml.) and, 0.64 volume of isopropyl alcohol was added and mixed gently. This solution was transferred to Sorvall centrifuge bottles and the precipitates collected by centrifugation at 10,000 rpm in a Sorvall GSA rotor and centrifuge. The precipitates were air dried and then gently resuspended in TE to a final volume of 100 ml.

About 40 mg. of RN'ase A (obtained from Sigma, St. Louis, Missouri) was suspended in 1 ml. TE, boiled for two minutes, added to the above DNA suspension and then the mixture was incubated at 37° C. for 15 hours. Next, an equal volume of buffer saturated phenol was added to the mixture and the phases separated by centrifugation (5,000 rpm, GSA rotor, 10 min.). The aqueous layer was decanted into a 250 ml. graduated cylinder and adjusted to 0.3M NaOAc by the addition of 3M NaOAC (pH 8.0). This solution was placed on ice and 2 volumes of cold ethanol was gently added to avoid mixing the two liquids. Using a procedure developed by Marmur et al., 1961, J. Mol. Biol. 3:208-218, the high molecular weight DNA species were collected by gently swirling a glass rod at the interface between the DNA and ethanol. The thus collected DNA was washed once in 70% ethanol and air dried prior to resuspension in 5 ml. TE supplemented to 0.1M NaCl to a final concentration of 1.4 mg./ml.

B. Collection of High Molecular Weight Fractions

Approximately one-half ml. of the DNA suspension from part A above was layered onto the top of four SW40 Beckman polyallomer tubes containing a 5-20% w/v sucrose gradient made in substantial accordance with the teaching of Example 1C with the exclusion of ethidium bromide and the substitution of 5% w/v and 20% w/v sucrose solutions for the respective 10% w/v and 40% w/v sucrose solutions. These gradients were run for 17 hours at 30,000 rpm using a Beckman SW40 rotor in a Beckman ultracentrifuge. One-half ml. fractions were collected from each tube by puncturing the bottom of the tube and collecting the drops. The fractions were examined by AGE and the high molecular weight fractions (>50 kb) were pooled and precipitated by conventional methods. The DNA precipitate was resuspended in 500 μl. TE to a final concentration of 1.4 μg./μl.

C. Preparation of the *Streptomyces fradiae* Insert DNA

About 0.5 ml. of the DNA from the preceding example was adjusted to 0.3M NaOAc by the addition of 3M NaOAc and precipitated with 2 volumes cold ethanol and stored at −20° C. overnight. The precipitate was collected by centrifugation, washed in ethanol and resuspended in 1.6 μl. TE overnight to a final concentration of 0.46 μg./μl. Three reactions were set up to digest the DNA with HaeIII restriction enzyme and three reactions were set up to digest the DNA with AluI restriction enzyme.

1. HaeIII Restriction Enzyme Digestions

The HaeIII reaction mixture was set up containing about 540 μl. of the suspended DNA, 250 μl. 10X HaeIII buffer (500 mM NaCl, 60 mM MgCl$_2$, 60 mM β-mercaptoethanol), 1700 μl. water, and 8.9 μl. of a 1/10 dilution of HaeIII enzyme (7 units/μl. BRL) in 1X HaeIII buffer. Three reactions, each containing ~880 μl., were prepared from the single HaeIII reaction mixture and incubated at 37° C. for 20 minutes, 40 minutes, and 60 minutes and then placed on ice. The extent of digestion was monitored by AGE. To each reaction, 2 μl. of a 1/10 dilution of HaeIII restriction enzyme was added and incubation for 30 minutes at 37° C. continued. The reactions were again placed on ice and the extent of digestion was monitored by AGE. This 2 μl. enzyme addition was repeated, and the extent of the final digestion was monitored by AGE. The three reactions were pooled together, made 0.3M NaOAc by the addition of 3M NaOAc, rinsed with 2 volumes ethanol and precipitated overnight at −20° C.

2. AluI Restriction Enzyme Digestions

The same procedure with respect to the HaeIII digestions was used for a similar digestion with AluI except that 10 μl. of a 1/10 dilution of AluI (6 units/μl. BRL), ~1700 μl. of distilled water and 10X AluI buffer (500 mM Tris-HCl pH 8.0, 50 mM MgCl$_2$, 500 mM NaCl, and 10 mM dithiothreitol) were used in place of the HaeIII restriction enzyme and buffer. The three reactions were run in substantial accordance with the teaching of the HaeIII digestions with the exception that only one additional incubation period with AluI enzyme was required. These reactions then were pooled and precipitated.

The two DNA digestions were separately collected by centrifugation (12,000 rpm, 12 mins.) in a HB4 rotor. The precipitates were washed once with 70% ethanol. Finally the precipitates were resuspended separately in 200 μl. TE, mixed and TE was added to a final volume of 600 μl. About 200 μl. of this pooled DNA was added to each of three, 13 ml. 5-20% w/v sucrose gradients. These three gradients were run for 17 hours in a SW40 Beckman rotor at 30,000 rpm at 5° C. About 30 fractions, containing ~0.4 ml. each, were collected from each tube by puncturing the bottoms of the gradient tubes and collecting drops. Each fraction was analyzed on AGE and those corresponding to DNA in the size range of 10-25 kb DNA were pooled and precipitated by conventional methods. The precipitate was resuspended in 800 μl. TE at a concentration of 0.065 μg./μl.

3. Methylation of *Streptomyces fradiae* DNA

About 200 μl. of 5 X EcoRI methylase buffer (500 mM Tris-HCl pH 8.0, 12.5 mM Dithiothreitol, 25 mM EDTA, 2 mg./ml. BSA, and 5.5 μM S-adenyl-methionine) and 10 μl. EcoRI methylase (10 units/μl. BRL) were added to the ~800 μl. of DNA prepared above and then incubated at 37° C. for 2 hours. The DNA was extracted twice with buffer saturated phenol and the phenol was re-extracted with TE. The aqueous phases were pooled and extracted twice with ether and then precipitated with sodium acetate followed by two volumes of ethanol and incubated at −20° C. for 2 hours.

The precipitate was collected by centrifugation (12,000 rpm, 15 mins.) and the DNA washed once in 70% ethanol, air dried, and then resuspended in 75 μl. of TE. This contained approximately 44 μg. of methylated-AluI-HaeIII partially digested *S. fradiae* DNA.

4. Linker Addition

About 40 μl. of EcoRI linker (pGGAATTCC obtained from Collaborative Research, Inc., 128 Spring Street, Lexington, Mass. 02173) at 100 μg./ml. in TE was incubated at 65° C. for three minutes and then cooled on ice. A ligation reaction containing 70 μl. of methylated *Streptomyces fradiae* DNA, 40 μl. linker DNA, 40 μl. 5X ligase/kinase buffer (250 mM Tris-HCl pH 7.8, 25% Glycerol, 25 mM Dithiotreitol, and 50 mM $MgCl_2$), 40 μl. 0.66M ATP and 12 μl. (1 unit/μl. BoehringerMannheim Biochemicals) T4 DNA ligase were incubated at room temperature for 12 hours. The reaction was terminated by increasing the temperature to 65° C. for five minutes and then stored at 4° C. overnight. About 190 μl. of the stored ligation reaction was mixed with 45 μl. 10X EcoRI buffer, 195 μl. distilled water and 20 μl. EcoRI enzyme (10 units/μl. BRL) and incubated at 37° C. for five hours. After the addition of 20 μl. 0.25M EDTA (pH 8.0), the reaction was terminated by increasing the temperature to 65° C. for five minutes followed by cooling on ice. This reaction was layered onto a 5–30% w/v sucrose gradient and run in a SW40 rotor (18 hours, 30,000 rpm, 5° C.). The tube was punctured at the bottom and 36 five drop fractions were collected. The fractions were examined by AGE and those fractions ranging in size from 10 to 19 kb were pooled, precipitated with sodium acetate and ethanol and stored overnight at −20° C. The DNA precipitates were collected by centrifugation in a Sorvall HB4 rotor (12,000 rpm, 15 min.), washed once in 70% ethanol, air dried and resuspended in 400 μl. TE. This suspension constitutes the EcoRI linked *S. fradiae* DNA at a concentraton of 0.022 μg./μl.

EXAMPLE 3

Production of Phage Library

About 2 μg. of the *Streptomyces fradiae* insert DNA, prepared in Example 2(C)(4), was mixed with 17.2 μl. (~3 μg.) Charon 4 arms, prepared in Example 1C, and then the DNA was precipitated by the addition of 3M sodium acetate to a final concentration to 0.3M NaOAc and two volumes of ethanol. This mixture was incubated at −70° C. The DNA pellet was collected by centrifugation in a Brinkman microfuge for 10 minutes, washed in 70% ethanol and air dried. Next, the pellet was resuspended in 16 μl. of the following ligation reaction mixture: 4 μl. kinase/ligase buffer, 10 μl. 0.66M ATP pH 7.4, 5 μl. distilled water, and 1 μl. T4 DNA ligase; this ligation reaction was incubated at 9° C. for 72 hours.

The ligation was conventionally packaged using Bethesda Research Laboratory packaging extract in substantial accordance with the manufacturer's specification. Other such in vitro packaging mixes, such as, Biotec packaging kit, are available for use in the present application. The packaging extract was loaded onto a CsCl block gradient and run in a SW50 Beckman rotor (2 hours, 30,000 rpm, 5° C.). The cesium chloride gradients were made in substantial accordance with the teaching of Maniatis et al., 1982, except that the density per 0.5 ml. of CsCl were 1.7, 1.5 and 1.3. The tube was punctured at the bottom and 10-drop fractions were collected and dialyzed individually in a BRL minidialysis unit against lambda buffer. The fractions were titered as described in Example 1A using a 10 ml. culture of *E. coli* K12 294 (ATCC 31446) in TMM overnight at 37° C. instead of *E. coli* K12 C600$R_k$-$M_k$-(ATCC 33525) and examined for recombinants. Recombinants were selected by the appearance of non-blue plaques as revealed on T plates (tryptone) supplemented with 10 mM $MgSO_4$ and 40 μg./ml. 5-Bromo-4-chloro-3-indolyl-β-D-galactosidase (X-gal from BRL). The various fractions were pooled to give a library of recombinant phages. Amplification of the primary lysate was made by preparing plate lysates of the library on *E. coli* K12 294 where at least 4,000 recombinant plaques were on each plate. From these plate lysates a large scale phage lysate and DNA prep were done as taught in Example 1. The DNA was resuspended in 1 ml. TE at a concentration of 0.23 μg./μl.

EXAMPLE 4

Culture of *E. coli* K12 C600$R_k$-$M_k$-/pHJL210 and Isolation of Plasmid pHJL210

A single bacterial colony of *E. coli* K12 C600$R_k$-$M_k$-/pHJL210 (NRRL B-15824) was inoculated into LB medium which contains, per liter aqueous solution, 10 g. Bacto tryptone, 5 g. Bacto yeast extract and 10 g. NaCl (pH 7.5) with 25 μg./ml. of ampicillin according to conventional microbiological procedures. The culture was incubated at 37° C. overnight. The following morning, 500 ml. of M9 medium (Miller et al., 1979, Experiments in Molecular Genetics, Cold Spring Harbor Laboratories, Cold Spring Harbor, N.Y.) supplemented to 1 mM $MgSO_4$, 0.2% glucose, 0.3–0.4% CAA (casamino acids, Difco), 2 μg./ml. B1 (thiamine-HCl, Sigma) and additives were inoculated with 5 ml. of the overnight culture. The culture was incubated with vigorous shaking at 37° C. overnight and the next morning samples of the overnight culture were inoculated at dilutions of 1/10 to 1/50 into the supplemented M9 media and incubated with vigorous shaking at 37° C. for 2½ to 3 hours. The turbidity of the culture measured with the blue filter was approximately 300 to 400 Klett units. Chloramphenicol (150–175 μg./ml.) was added to the culture and incubation with vigorous shaking was continued overnight.

The bacterial cells were harvested by centrifugation at 7500 rpm for 5 minutes at 4° C. and then washed twice with 200 ml. of SV (0.15M NaCl, 0.1M NaEDTA pH 8.0). The pellet was resuspended in 10 ml./gm. wet weight TS solution (25% sucrose, 50 mM Tris, pH 8) and placed on ice. To this suspension, 2 ml./gm. wet weight of lysozyme solution (5 mg./ml. in 50 mM Tris-HCl pH 7.8) was added and left to chill on ice for 5 minutes. Next, 4 ml./gm. wet weight of 0.25 M EDTA pH 8.0 was added and chilled for another 5 minutes. Upon the addition of 16 ml./gm. wet weight lysis solution (0.4% deoxycholate, 1% Brij 58, 50 mM Tris and 0.0625 M EDTA, pH 8) the mixture was incubated at 37° C. for 15–30 minutes. The DNA was recovered by centrifugation in a Sorvall SS34 rotor at 21,000 rpm for 15–30 minutes at 4° C. The supernatant was saved and 0.1 vol. of 3 M NaOAc, at pH 8 and 0.64 volumes isopropyl alcohol were added to the supernatant. The solution was centrifuged at 10,000 rpm for 10 minutes at 4° C., whereupon the pellet was resuspended in 0.1 volume TE (10 mM Tris, 1 mM EDTA pH 8). The plasmid DNA was purified by centrifugation to equilibrium in cesium chloride (CsCl) density gradients containing propidium diiodide according to known techniques.

EXAMPLE 5

Subcloning *Streptomyces fradiae* DNA

A. Preparation of Plasmid pHJL210

About 10 μl. (~11 μg.) of plasmid pHJL210 (prepared in Example 4) was added to 5 μl. 10X EcoRI buffer, 5 μl. BSA, 25 μl. distilled water and 5 μl. of EcoRI restriction enzyme (10 units/ml NEB) and incubated for two hours at 37° C. The reaction was terminated by raising the temperature to 70° C. for 10 minutes. The DNA was precipitated by addition of 6 μl. 3M NaOAc pH 8.0 and 120 μl. cold ethanol. After incubation at −70° C. for 15 minutes, the DNA was collected by centrifugation in a Brinkman microfuge for 10 minutes. The DNA pellet was washed once with 70% ethanol, air dried and then resuspended in 80 μl. distilled H$_2$O. This suspension was supplemented with 20 μl. 5 X CIAP buffer (500 mM Tris-HCl pH 7.5, 250 mM NaCl and 50 mM MgCl$_2$). To dephosphorylate the DNA, 3 μl. of a 1/10 dilution of calf intestinal alkaline phosphatase, Grade III (4 units/μl. Boehringer Mannheim) prepared in accordance with the manufacturer's specification, was added and the reaction incubated first at 37° C. for 30 minutes and then at 70° C. for an additional 30 minutes. A restriction site and functional map of plasmid pHJL210 is presented in FIG. 1 of the accompanying drawing.

B. Preparation of the *Streptomyces fradiae* DNA Library

About 50 μl. (~11.5 μg.) of the DNA from the lambda library (prepared in Example 3) was incubated with 10 μl. EcoRI buffer, 10 μl. BSA, 25 μl. water, and 5 μl. EcoRI enzyme (10 units/ml. NEB) for three hours at 37° C. The reaction was terminated by increasing the temperature to 70° C. for 10 minutes. About 5 μl. of this reaction was examined by AGE to verify the results of complete digestion.

C. Ligation

About 20 μl. of the dephosphorylated and EcoRI-digested pHJL210 DNA was added to ~95 μl. EcoRI-digested library DNA and the mixture precipitated with 12 μl. 3M NaOAc and 240 μl. cold 100% ethanol. After incubation at −70° C. on dry ice for 10 minutes, the precipitate was collected by centrifugation, washed once with 70% ethanol and air dried. The pellet was resuspended in 58 μl. distilled water and to this solution, 100 μl. 0.66M ATP, 40 μl. 5 X kinase/ligase buffer and 2 μl. ligase (Boehringer-Mannheim) were added and the ligation incubated at 15° C. for 20 hours. The ligation was diluted to promote circularization by the additions of ~169 μl. distilled water, 80 μl. 5X kinase/ligase buffer, 150 μl. 0.66M ATP and 1 μl. ligase. The solution was incubated for 72 hours at 15° C. and then the reaction terminated by raising the temperature to 70° C. for 10 minutes. The DNA was precipitated by dividing the reaction equally into two large Eppenforf tubes and adding 30 μl. 3M NaOAc and 660 μl. cold ethanol to each tube. Both tubes were incubated on dry ice for 10 minutes and then the DNA was collected in a Brinkman microfuge, washed once with 70% ethanol, air dried and finally each was resuspended in 140 μl. TE. They were pooled to give a final volume of 280 μl. in TE.

EXAMPLE 6

Transformation of *Streptomyces griseofuscus*

A. Growth of Cultures for Preparation of Protoplasts

A vegetative inoculum was conventionally prepared by growing *Streptomyces griseofuscus*, a strain deposited and made part of the permanent stock culture collection of the American Type Culture Collection, Rockville, Md. 20852, from which it is available to the public under the accession number ATCC 23916, under submerged conditions for 20 hours at 30° C. in TSB supplemented with 0.4% glycine. The procedure for protoplasting *S. griseofuscus* is time-consuming and was generally performed as follows. Streak out *S. griseofuscus* on a plate containing YMX agar (0.3% yeast extract, 0.3% malt extract, 0.2% dextrose and 2% agar. Approximately 48 hours later, inoculate a single bacterial colony into 10 ml. TSB; homogenize and incubate at 30° C. overnight. Next, homogenize 4 ml. of the overnight culture and add 100 ml. TSB supplemented with 0.4% glycine and incubate overnight at 30° C. Repeat this procedure the following afternoon using fresh overnight culture. Harvest the cells in a bench top centrifuge and wash three times in 100 ml. of 10.3% sucrose. Resuspend the cell pellet in 100 ml. of P medium (Hopwood and Wright, 1978, J. Molecular and General Genetics 162:307) supplemented with lysozyme (1 mg./ml.) and incubate at 30° C. for 2 hours. Centrifuge to pellet the protoplasts and wash the pellet three times in 100 ml. P medium, vortexing and pipetting the pellet into solution at each wash. Resuspend the final pellet in 10 ml. P medium for subsequent transformation.

B. Transformation

About 10 μl. of plasmid DNA containing *Streptomyces fradiae* DNA in ligation buffer and about 150 μl. of *S. griseofuscus* protoplasts were mixed slightly in a test tube. To this mixture about 101 μl. 50% PEG 1000 (polyethylene glycol, Sigma) in P medium was added and pipeted to mix. After a 1–2 minute wait, P medium was added to bring the volume up to 1 ml. The transformed cells were plated on R2 medium (Baltz et al., 1981, J. Gen. Microbiol. 127:137-146) and incubated overnight at 30° C. The regenerating protoplasts were overlayed with 3 ml. R2 overlays containing 400 μg./ml. thiostrepton and incubated at 30° C. for at least 4 days. This procedure was repeated 27 times until all of the ligation reaction mixture was used. The resulting ~5,000 thiostrepton-resistant *S. qriseofuscus* transformants represent a mixture of recombinants: *Streptomyces fradiae* DNA into plasmid pHJL210; lambda pieces in a very small proportion (lambda stuffers into plasmid pHJL210); and some cloning vectors. These colonies were scraped into TSB and 10% glycerol (225 ml.) and the suspension was homogenized and aliquoted out to be frozen either at −20° C. or under liquid nitrogen (vapor phase). These cell preservations contain approximately 1 x $10^7$ colony forming units/ml. and was estimated to be 60% recombinants.

EXAMPLE 7

Screening and Selection Analysis

A. Screen for Tylosin Resistant Clones

Figure 2:
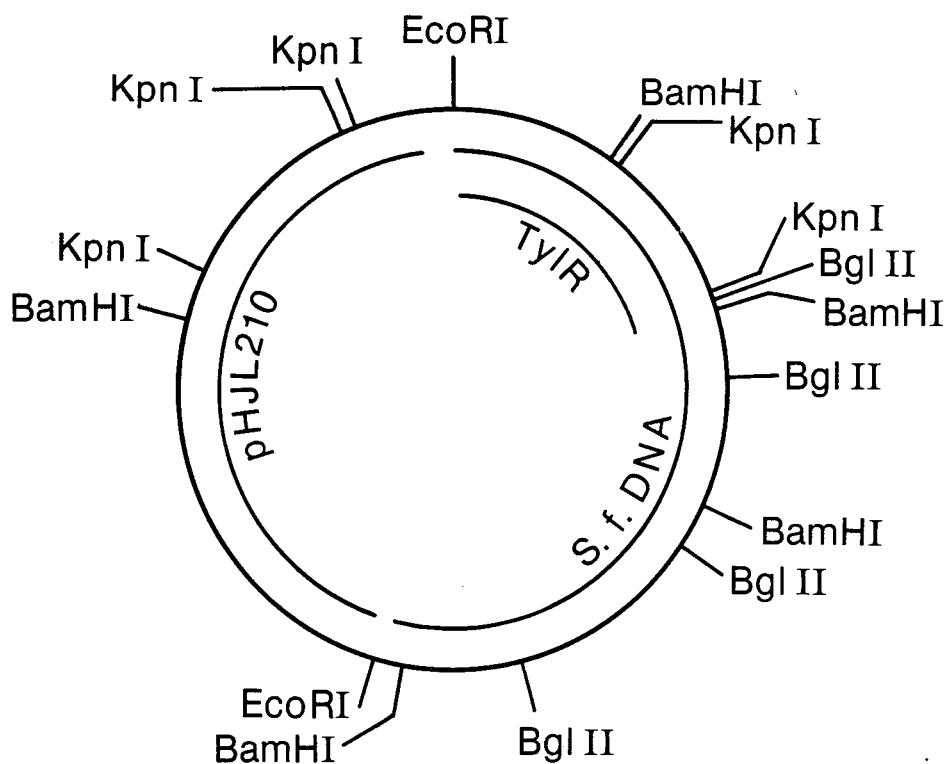
FIG. 2 is a restriction site and functional map of plasmid pHJL240.

We determined that *Streptomyces griseofuscus* was very sensitive to the macrolide tylosin at levels of 50 μg./ml. on YMX agar plates. In fact, nitrosoguanidine mutagenization *S. griseofuscus* does not generate mutants that will plate on tylosin. With this knowledge we plated 1 ml. of the preserved *S. griseofuscus* transformants on ten YMX agar plates containing thiostrepton (40 μg./ml.) and tylosin (50 μg./ml.). After incubation for four days at 30° C. approximately 2000 colonies were present. These colonies were verified as tylosin-resistant at concentrations up to 500 μg./ml. The DNA from twelve of the recombinants was isolated and back-transformed into *E. coli* K12 C600R$_k$—M$_k$—. These were found to all contain the same plasmid, pHJL240, which contains an ~13 kb EcoRI insert into plasmid pHJL210. Plasmid pHJL240 can be conventionally isolated from *E. coli* K12 C600R$_k$—M$_k$—/pHJL240, a strain deposited and made part of the stock culture collection of the Northern Regional Research Laboratory, Peoria, Ill. 61604. It is available to the public as a source and stock reservoir of the plasmid under the accession number NRRL B-15886. Southern hydridization (performed in accordance with the teaching of Fishman et al., 1983, J. Bacteriol. 155:459-466) revealed that the ~13 kb EcoRI insert was derived from the *S. fradiae* genome. A restriction site and functional map of plasmid pHJL240 is presented in FIG. 2 of the accompanying drawings.

We claim:

1. A method for converting naturally-occurring Streptomycetes DNA, said DNA incapable of being cloned into a restrictionless heterospecific host because of the presence of nucleotides other than adenine, guanine, cytosine, on thymine, said method comprising:
    (a) inserting said naturally-occurring DNA into a bateriophage cloning vector and transforming a bacterial host cell with said vector, said vector being capable of replication in said host cell, and
    (b) growing said bacterial host cell transformed with bateriophage cloning vector of step (a) under conditions suitable for replicating and thereby converting said naturally-occuring a replicated DNA consisting of nucleotides selected from the group consisting of adenine, guanine, cytosine, and thymine.

2. A method of claim 1 wherein said bacteriophage is from the group consisting of Charon phage vectors.

3. A method of claim 2 wherein said Charon phage vector is Charon 4.

4. A method of claim 1 wherein said modified Streptomycetes DNA is from *Streptomyces fradiae*.

5. The method of claim 1 which further comprises ligating the relicated DNA of step (b) into a recombinant DNA cloning vector that is capable of replication and selection in an organism selected from the group consisting of E. coli and Streptomycetes.

6. A method of claim 5 wherein said recombinant DNA cloning vector is plasmid pHJL210.

7. A method of claim 5 wherein the Streptomycetes is *Streptomyces griseofuscus*.

8. The transformed Streptomycetes which is *Streptomyces griseofuscus*/pHJL240.

9. A recombinant DNA plasmid pHJL240.

* * * * *

UNITED STATES PATENT AND TRADEMARK OFFICE
CERTIFICATE OF CORRECTION

PATENT NO. : 4,710,466

DATED : December 1, 1987

INVENTOR(S) : Charles L. Hershberger and Jeffrey L. Larson

It is certified that error appears in the above-identified patent and that said Letters Patent is hereby corrected as shown below:

Claim 1, line 5, "on" should read -- or --.

Claim 1, line 7, "bateriophage" should read -- bacteriophage --.

Claim 1, line 13, "naturally-occurring a replicated DNA" should read -- naturally-occurring DNA into a replicated DNA --.

Claim 5, line 2, "relicated" should read -- replicated --.

Signed and Sealed this

Thirteenth Day of September, 1988

Attest:

DONALD J. QUIGG

*Attesting Officer*          *Commissioner of Patents and Trademarks*